(12) United States Patent
Ashiba et al.

(10) Patent No.: US 12,239,338 B2
(45) Date of Patent: Mar. 4, 2025

(54) TREATMENT DEVICE WITH DAMPING FEATURE

(71) Applicant: OLYMPUS MEDICAL SYSTEMS CORP., Tokyo (JP)

(72) Inventors: Hiroshi Ashiba, Tokorozawa (JP); Yasuhiro Maeda, Mitaka (JP); Minoru Katsumata, Fuchu (JP); Keisuke Nagao, Kokubunji (JP)

(73) Assignee: Olympus Medical Systems Corp., Tokyo (JP)

( * ) Notice: Subject to any disclaimer, the term of this patent is extended or adjusted under 35 U.S.C. 154(b) by 556 days.

(21) Appl. No.: 17/558,665

(22) Filed: Dec. 22, 2021

(65) Prior Publication Data
US 2022/0265306 A1 Aug. 25, 2022

Related U.S. Application Data

(60) Provisional application No. 63/152,899, filed on Feb. 24, 2021.

(51) Int. Cl.
*A61B 17/32* (2006.01)

(52) U.S. Cl.
CPC .............. *A61B 17/320092* (2013.01); *A61B 2017/320088* (2013.01); *A61B 2017/320094* (2017.08)

(58) Field of Classification Search
CPC .... A61B 17/320092; A61B 17/320068; A61B 2017/320088; A61B 2017/320094; A61B 2017/320069; A61B 2017/320071; A61B 2017/320072; A61B 2017/320082; A61N 7/00

See application file for complete search history.

(56) References Cited

U.S. PATENT DOCUMENTS

| 5,989,275 | A | 11/1999 | Estabrook et al. |
| 8,696,666 | B2 | 4/2014 | Sanai et al. |
| 10,098,655 | B2 | 10/2018 | Miyajiri et al. |
| 2005/0033201 | A1* | 2/2005 | Takahashi ...... A61B 17/320068 601/2 |

(Continued)

FOREIGN PATENT DOCUMENTS

| JP | 6084349 B1 | 2/2017 |
| WO | 2016/163450 A1 | 10/2016 |

OTHER PUBLICATIONS

Office Action dated Jul. 21, 2023, issued in corresponding European Patent Application No. 22155755.6.

(Continued)

*Primary Examiner* — Ankit D Tejani
*Assistant Examiner* — Joshua Brendon Solomon
(74) *Attorney, Agent, or Firm* — Morgan, Lewis & Bockius LLP

(57) ABSTRACT

Treatment device for ultrasonic treatment and high frequency treatment procedure is equipped with an ultrasonic transducer including piezoelectric elements converting electrical power into ultrasonic vibrations. The treatment device includes a transmission rod with a treatment probe and jaw for clasping objects. The transmission rod includes one or more features for damping, to minimize or prevent excess vibrations and to, among other things, decrease frictional heat caused by the friction between the damping features and the transmission rod arising from attenuating the ultrasonic vibrations.

20 Claims, 8 Drawing Sheets

(56) References Cited

U.S. PATENT DOCUMENTS

| | | | |
|---|---|---|---|
| 2008/0058845 A1* | 3/2008 | Shimizu | A61B 17/29 |
| | | | 606/205 |
| 2012/0109184 A1* | 5/2012 | Spivey | A61B 17/00234 |
| | | | 606/205 |
| 2016/0235432 A1* | 8/2016 | Akagane | A61B 18/1442 |
| 2016/0278804 A1 | 9/2016 | Akagane et al. | |
| 2017/0119425 A1 | 5/2017 | Hibner et al. | |
| 2017/0215913 A1 | 8/2017 | Miyajiri et al. | |
| 2018/0042638 A1 | 2/2018 | Hirai et al. | |

OTHER PUBLICATIONS

Office Action dated Jan. 31, 2023, issued in corresponding Japanese Patent Application No. 2022-015785.
Extended European Search Report issued on Jun. 23, 2022 in European Patent Application No. 22155755.6.

\* cited by examiner

TREATMENT DEVICE WITH DAMPING FEATURE

RELATED APPLICATION DATA

This application is based on and claims priority under 35 U.S.C. § 119 to U.S. Provisional Application No. 63/152,899 filed on Feb. 24, 2021, the entire contents of which are incorporated herein by reference.

FIELD OF DISCLOSURE

The present disclosure relates to an ultrasonic treatment device used for dissecting and coagulating tissues. The ultrasonic treatment device is equipped with an ultrasonic transducer including piezoelectric elements converting electrical power into ultrasonic vibrations. The ultrasonic vibrations are transmitted along the transmission member to a probe that serves to clasp objects together with a jaw for the performance of treatment procedures on biological tissue of patients, such as blood vessel sealing. The transmission member may create undesired transverse vibration that causes problems such as deterioration of blood vessel sealing performance, heat generation, abnormal stress, and abnormal noise.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

FIG. 12 is a figure of an ultrasonic treatment device in the related art (U.S. Pat. No. 8,696,666). The related art surgical operation system 1 consists of a handpiece 2, a main body apparatus 3 which is an output control apparatus, a foot switch 4 and a counter electrode plate 5. The handpiece 2 is a surgical treatment instrument capable of treatment using both ultrasonic and high-frequency current. The handpiece 2 is connected to the main body apparatus 3 via a cable 2a which is attachable and detachable. The handpiece 2 has an insertion portion 2b and a handle portion 2c. The connector portion 3a connects the handpiece to the main body apparatus 3, which controls the output of the ultrasonic vibration and/or high-frequency current. The main body apparatus 3 has a plurality of displays 3b and a plurality of various operation buttons 3c for controlling the performance of handpiece 2. The foot switch 4 is connected to the main body apparatus 3 through a cable 4 a, and switches the mode from treatment using ultrasonic vibration, treatment using high-frequency current, or treatment using both. The counter electrode plate 5 is connected to the main body apparatus 3 through a cable 5 a. The counter electrode plate 5 is a return electrode for returning a current which passes through a subject at the time of monopolar output of a high-frequency current.

FIG. 13 is a figure of a portion of an ultrasonic treatment device in the related art (U.S. Pat. No. 5,989,275). The related art ultrasonic treatment device includes a transmission rod 86 used for transmitting ultrasonic vibrations to the ultrasonic probe. The transmission rod 86 is covered by a damping sheath 160, which is further covered by the elongated tubular member 174. Diametrically opposed openings 162b and 162c, as well as longitudinal slit 164 are formed on the damping sheath 160. Compliant members 190b and 190c (O-rings and fenders) are disposed around the periphery of the damping sheath 160, which are preferably disposed around the nodes to minimize damping of the desired longitudinal vibration.

The damping sheath 160 is constructed of a polymeric material, preferably with a low coefficient of friction to minimize dissipation of energy from the axial motion or longitudinal vibration of the transmission rod 86. The damping sheath 160 is preferably in light contact with the transmission rod 86 to dampen or limit non-axial or transverse side-to-side vibration of the transmission rod 86. The damping sheath 160 can dampen transverse motion of the unwanted vibration which are located randomly along the length of the transmission rod 86 relative to the nodes and antinodes of the desired longitudinal vibration.

Horizontal vibrations occurring in ultrasonic treatment devices when the ultrasonic probe is vibrated can lead to problems, such as deterioration of blood vessel sealing performance, heat generation, abnormal stress, and abnormal noise. Even though related art ultrasonic treatment devices may have structures, such as the damping sheath 160, such a damping sheath 160 is in contact throughout the transmission rod 86 at all times in areas where dampening or limiting the non-axial or transverse side-to-side vibration is not necessary. For instance, when the related art ultrasonic treatment device is operated and clasps and objects such as human tissues during the treatment procedure, the need for damping the transverse vibrations occurring at the ultrasonic probe decreases since the direct contact made between the ultrasonic probe and the human tissue or the other clasping feature results in damping of the transverse vibration. Furthermore, the contacting of the damping sheath 160 and the ultrasonic probe causes rise in the electric power and frictional heat during the treatment procedure using the longitudinal vibration. Therefore, a configuration is preferred in which damping occurs when the ultrasonic probe is not used for clasping but does not occur when the ultrasonic probe is used for clasping human tissues.

SUMMARY

Accordingly, there is a need for designing an ultrasonic treatment device with an efficient structure in view of the practical usage, which would substantially obviate one or more of the issues due to limitations and disadvantages of related art treatment devices. An object of the present disclosure is to provide an improved treatment device having an efficient structure and practical administration of the associated medical procedure. For example, there is a need to provide improved damping solutions that, for example, minimize the contact between a transmission rod and a damping structure, so as to minimize or prevent heat generation, abnormal noise, or other issues to arise. At least one or some of the objectives is achieved by the treatment device disclosed herein.

Additional features and advantages will be set forth in the description that follows, and in part will be apparent from the description, or may be learned by practice of the invention. The objectives and other advantages of the disclosed treatment device will be realized and attained by the structure particularly pointed out in the written description and claims thereof, as well as the appended drawings.

In general, the disclosed structures and systems provide for an ultrasonic treatment device efficiently suppressing problems such as heat generation, abnormal stress, and abnormal noise created from vertical and/or horizontal ultrasonic vibrations. The treatment device for ultrasonic treatment and high frequency treatment procedure is equipped with an ultrasonic transducer including piezoelectric elements converting electrical power into ultrasonic vibrations. The treatment device includes a transmission rod with a treatment probe and jaw for clasping objects, such as biological tissue of a patient. The treatment device can includes features for damping transverse vibrations associated with the ultrasonic vibrations, such as a sheath on a portion of the transmission rod or treatment probe, an outer surface of the treatment probe configured to contact an inner surface of a surrounding structure (such as the probe holder), an outer surface of the transmission rod configured to contact an inner surface of a surrounding structure (such as the sheath of the treatment device), or combinations of such features. Damping transverse vibrations minimizes or prevents excess vibrations and, among other things, decreases frictional heat caused by the damping features attenuating the ultrasonic vibrations.

In the exemplary embodiments, the damping feature is associated with the probe holder, which is a structure that at least partially circumscribes the outer circumference surface of the treatment probe and through which the treatment probe can slidably move. Movement of the jaw between an open position (when the jaw is not in contact with a surface of the treatment probe) and a closed position (when the jaw is in contact with a surface of the treatment probe) cause the outer circumference surface of the treatment probe to move from a first position in which the treatment probe is in contact with the damping feature (such as, for example, contacting a surface of the probe holder) and a second position in which the treatment probe is spaced apart from the damping feature (such as, for example, spaced apart from surfaces of the probe holder). By being in contact with the damping feature when the jaw is in the open position (which is otherwise an unloaded condition of the treatment probe), the damping feature suppresses transverse vibration of the treatment probe. Correspondingly, when the treatment probe is in a loaded condition by being in-use during a procedure, the jaw is in the closed position and the treatment probe is not in contact with the damping feature associated with the probe holder, for example, by the treatment probe being biased away from contacting a surface of the probe holder.

In other exemplary embodiments, the damping feature is associated with the drive member, which is a structure that slidably moves within the sheath of the treatment device to extend and retract the treatment probe and to actuate movement of the jaw. Movement of the drive member causes the treatment probe to move and also for the jaw to move between an open position (when the jaw is not in contact with a surface of the treatment probe) and a closed position (when the jaw is in contact with a surface of the treatment probe). The treatment probe is attached to the transmission rod at a transition region and, with rearward movement of treatment probe (i.e., in the retracting direction), a proximal end of the drive member moves toward and contacts the surface of the transition region of the transmission rod. A damping feature is located at the portion of the drive member that contacts the transition region. Thus, when moved in the retracting direction, the damping feature of the drive member is caused to contact the surface of the transition region of the transmission rod. By coordinating the movement of the drive member and the operation of the jaw so that the damping feature of the drive member is caused to be in contact with the surface of the transition region of the transmission rod when the jaw is in the open position (which is otherwise an unloaded condition of the treatment probe), the damping feature suppresses transverse vibration of the treatment probe. Correspondingly, movement of the drive member and the operation of the jaw can also be coordinated so that, when the treatment probe is in a loaded condition by being in-use during a procedure, the jaw is in the closed position and the damping feature of the drive member is not in contact with the surface of the transition region of the transmission rod, for example, by the drive member being slidably moved toward a distal end to separate the damping feature of the drive member from the surface of the transition region of the transmission rod.

Additionally, in some embodiments, the damping feature is provided integrally with the structure that opens and closes the jaw, and thereby switches the state of contact and separation between the damping feature and the transmission rod and/or treatment probe as the jaw is opened and closed. Still further, in some embodiments the damping features can be placed at either the antinode or the node of the ultrasonic vibrations.

Embodiments of the disclosed surgical treatment device comprises a transducer generating ultrasonic vibrations, a transmission rod including a treatment probe in which a proximal end of the transmission rod is operatively connected to the transducer for transmitting ultrasonic vibration generated by the transducer to the treatment probe located at the distal end, and the treatment probe including a treatment surface and a jaw moveable relative to the transmission rod from an open position to a closed position. The damping feature contacts the transmission rod when the jaw is in the open position and the damping feature is spaced apart from the transmission rod when the jaw is in the closed position.

In some embodiments, the damping feature is made of insulate material.

In some embodiments, the damping feature is made of resin.

In some embodiments, the damping feature is made of rubber.

In some embodiments, the damping feature covers the transmission rod perpendicularly as to the treatment surface.

In some embodiments, the damping feature is placed within half wavelength of the ultrasonic vibration from the distal end of the treatment probe in the axial proximal direction.

In some embodiments, the damping feature is placed near the fulcrum of the jaw.

In some embodiments, the transmission rod is displaced towards the direction the jaw closes in the closed position.

In some embodiments, the contact between the damping feature and transmission rod does not occur at a node of a transverse vibration of the ultrasonic vibration.

In some embodiments, the contact between the damping feature and transmission rod does not occur at an antinode of a longitudinal vibration of the ultrasonic vibration.

In some embodiments, the contact between the damping feature and transmission rod occurs at an antinode of a transverse vibration of the ultrasonic vibration.

In some embodiments, the treatment probe is configured to treat biological tissue.

In some embodiments, the treatment probe is configured as an electrode for treatment using high frequency currents.

In some embodiments, the damping feature prevents short circuit between the transmission rod and other parts of the treatment device.

In some embodiments, the treatment probe includes a curved shape.

In some embodiments, a surgical treatment device comprises a transducer generating ultrasonic vibrations, a transmission rod including a treatment probe in which a proximal end of the transmission rod is operatively connected to the transducer for transmitting ultrasonic vibration generated by the transducer to the treatment probe located at the distal end, the treatment probe including a treatment surface and a jaw moveable relative to the transmission rod from an open position to a closed position, and a slider that moves in a direction parallel with the transmission rod. The slider and jaw are configured so that, when the slider moves towards the proximal end of the transmission rod the jaw moves in the opening direction and, when the slider moves towards the distal end of the transmission rod the jaw moves in the closing direction. Furthermore, the slider includes a damping feature that contacts the transmission rod when the jaw is in the open position and the damping feature is spaced apart from the transmission rod when the jaw is in the closed position.

In some embodiments, the damping feature is made of insulate material.

In some embodiments, the damping feature is made of resin.

In some embodiments, the damping feature is made of rubber.

In some embodiments, the damping feature has a square or rectangular shape.

In some embodiments, the damping feature has a triangular shape.

In some embodiments, the damping feature contacts the transmission rod applying force in the radial direction.

In some embodiments, the damping feature moves integrally with the slider.

In some embodiments, the contact between the damping member and transmission rod does not occur at a node of a transverse vibration of the ultrasonic vibration.

In some embodiments, the contact between the damping member and transmission rod does not occur at an antinode of a longitudinal vibration of the ultrasonic vibration.

In some embodiments, the contact between the damping member and transmission rod occurs at an antinode of the transverse vibration of the ultrasonic vibration.

In some embodiments, the treatment probe is configured to treat biological tissue.

In some embodiments, the treatment probe is configured as an electrode for treatment using high frequency currents.

In some embodiments, the damping feature prevents short circuit between the transmission rod and other parts of the treatment device.

In some embodiments, the treatment probe includes a curved shape.

In some embodiments, the transmission rod includes a portion having a larger diameter compared to the other portions of the transmission rod.

In some embodiments, the diameter of the portion having a larger diameter gradually increases.

In some embodiments, a method for controlling a surgical treatment device is disclosed. The method comprises generating ultrasonic vibrations, connecting a transmission rod including a treatment probe to the transducer for transmitting ultrasonic vibration generated by the transducer to the treatment probe, moving the slider in a direction parallel with the transmission rod for opening and closing the jaw movable relative to the treatment surface of the transmission rod, and moving the slider and jaw are configured so that, when the slider moves towards the proximal end of the transmission rod the jaw moves in the opening direction and, when the slider moves towards the distal end of the transmission rod the jaw moves in the closing direction. Moving of the slider includes a damping feature that contacts the transmission rod when the jaw is in the open position, and moving of the damping feature is spaced apart from the transmission rod when the jaw is in the closed position.

Other systems, methods, features and advantages will be, or will become, apparent to one with skill in the art upon examination of the following figures and detailed description. It is intended that all such additional systems, methods, features and advantages be included within this description, be within the scope of the present disclosure, and be protected by the following claims. Nothing in this section should be taken as a limitation on those claims. Further aspects and advantages are discussed below in conjunction with the embodiments of the disclosed input device. It is to be understood that both the foregoing general description and the following detailed description of the disclosed input device are examples and explanatory and are intended to provide further explanation of the disclosed input device as claimed.

BRIEF DESCRIPTION OF THE DRAWING

The following detailed description of preferred embodiments can be read in connection with the accompanying drawings in which like numerals designate like elements and in which.

Throughout all of the drawings, dimensions of respective constituent elements are appropriately adjusted for clarity.

DETAILED DESCRIPTION

Figure 1:
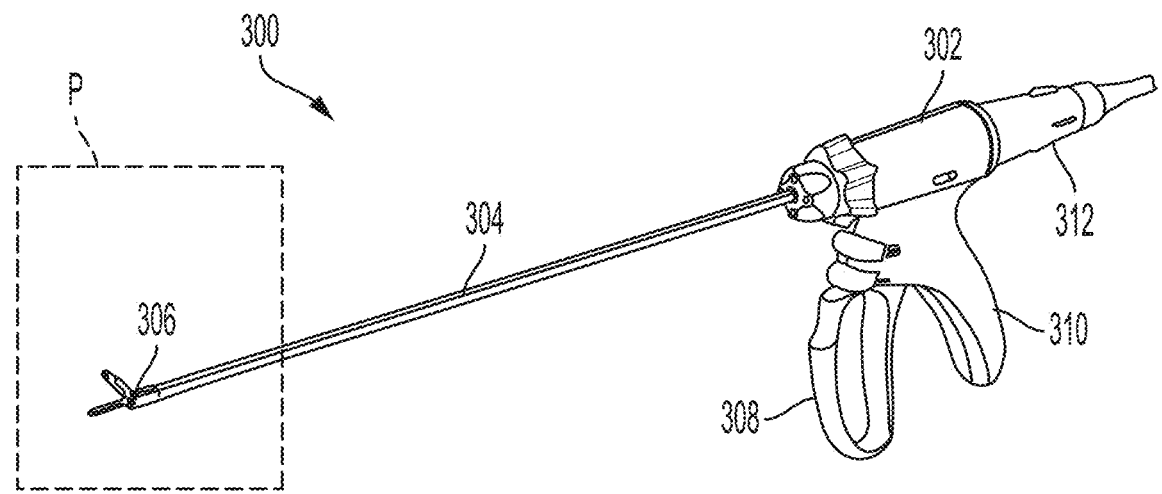
FIG. 1 shows an embodiment of a treatment device.

FIG. 1 is an illustration of a surgical treatment device 300 including a body 302, a sheath 304, and a treatment end 306. The body 302 includes a moving arm 308, a grip 310, and a transducer 312. The moving arm 308 is used together with grip 310 to actuate and operate the functions of treatment end 306. The transducer 312 includes an ultrasonic transducer which is connected to a power source supplying power used for ultrasonic treatment and/or high-frequency treatment using surgical treatment device 300. The power source can be a wired or wireless power source. The sheath 304 protects the wires and members contained therein, such as those used for operating the functions of treatment end 306.

Figure 2:
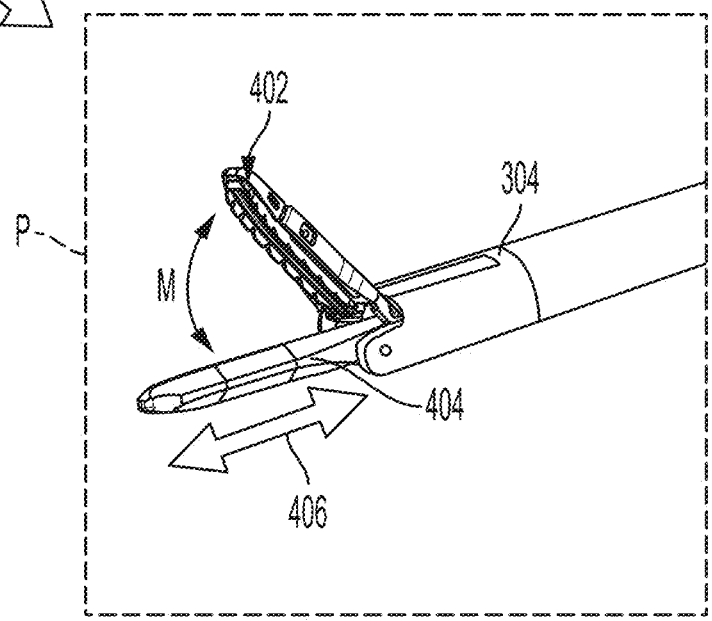
FIG. 2 shows a magnified view of the treatment end of the treatment device in Area P in FIG. 1.

FIG. 2 is the magnified view of the treatment end 306 of the surgical treatment device 300. The treatment end 306 consists of a jaw 402 and an ultrasonic probe 404. The jaw 402 moves (indicated by arrow M) relative to the ultrasonic probe 404 to open and close in the vertical direction through the manipulation of the movable handle 308 in order to clasp biological tissues and other objects for treatment. The ultrasonic probe 404 vibrates at an ultrasonic frequency transmitted through the transmission member within sheath 304. A longitudinal vibration, an ultrasonic vibration of the ultrasonic probe 404 made in the direction 406, creates frictional heat used for treatment purposes such as dissection of tissues, as well as frictional heat caused through contacting objects such as damping members. The ultrasonic probe 404 may have a curved shape and may also serves as an electrode for treatment using high frequency currents.

Figure 3A:
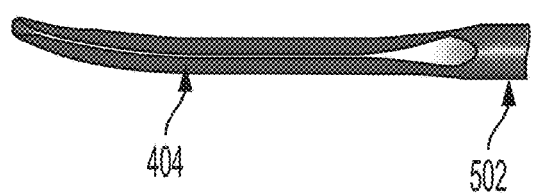
FIG. 3A is a top view of a treatment region of an ultrasonic probe and FIG. 3B is an exaggerated representation, based on a simulation, of the ultrasonic vibrations of the treatment region in transverse vibration mode.

FIG. 3A illustrates the ultrasonic probe 404 viewed from the vertical direction, the direction the jaw 402 opens and closes. FIG. 3A also illustrates the transmission member 502 extending in a distal direction from the ultrasonic probe 404, and which, within the arrangement of the treatment device, extends within the sheath 304 and connects to the transducer 312. The transmission member 502 is configured to transmit ultrasonic energy and/or high frequency energy from the transducer to the ultrasonic probe 404, which has a curved shape. In the FIG. 3A view, the ultrasonic probe 404 and transmission member 502 are in a stationary state, i.e., a state where neither the ultrasonic vibration nor the high frequency current is applied to the ultrasonic probe 404 and transmission member 502.

Figure 3B:
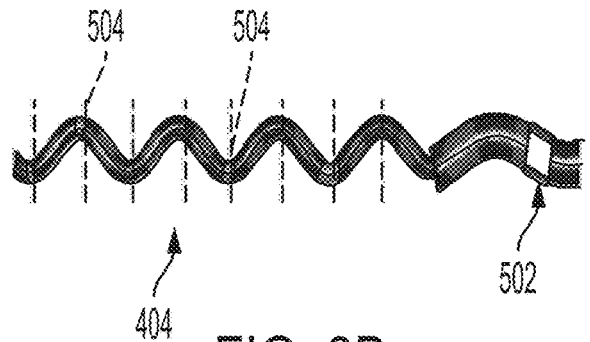

FIG. 3B also illustrates the ultrasonic probe 404 viewed from the vertical direction, the direction the jaw 402 opens and closes. FIG. 3B illustrates an exaggerated representation of the ultrasonic probe 404 and transmission member 502 in an oscillating state, i.e., a state where the ultrasonic vibration is applied.

Considering the use of ultrasonic probe 404 in treatment procedures, longitudinal vibration would be the desirable ultrasonic vibration. On the contrary, transverse vibrations and torsional vibrations would be undesirable ultrasonic vibrations that may cause issues during the treatment procedures. The longitudinal vibration occurs in parallel to the center axis of the ultrasonic probe 404 and the undesired transverse vibration occurs in the direction perpendicular to the center axis of the ultrasonic probe and the longitudinal vibration. Because the ultrasonic probe 404 is curved in the horizontal direction with an aim to improve the visibility during the treatment procedure, the axial unbalance of the ultrasonic probe 404 in the horizontal direction may create substantial transverse vibrations when the ultrasonic vibration is applied to the ultrasonic probe 404. In the case shown in FIG. 3B, the ultrasonic vibration has caused a transverse vibration that includes antinodes (indicated in FIG. 3B by dashed lines 504 at the local maxima and minima) periodically along the length of the ultrasonic probe 404. The transverse vibration at the antinode 504 of the transverse vibration leads to problems such as heat generation, abnormal stress, and abnormal noise, and thus need to be attenuated.

Figure 4A:
FIG. 4A is a side view of a treatment region of an ultrasonic probe and FIG. 4B is an exaggerated representation, based on a simulation, of the ultrasonic vibrations of the treatment region in transverse vibration mode.
Figure 4B:
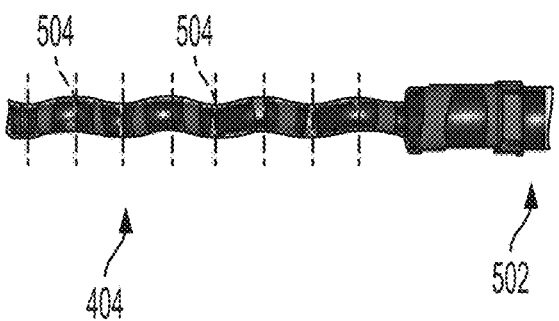
Figure 5:
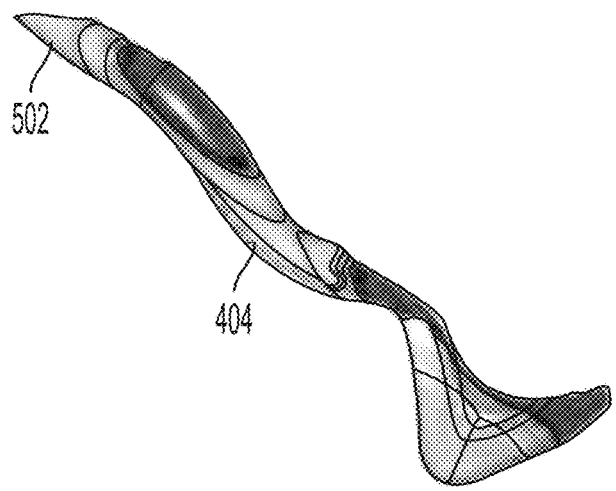
FIG. 5 is an exaggerated perspective view of a treatment region of an ultrasonic probe and showing the variation in transverse vibration during vibration of the ultrasonic probe.

FIG. 4A illustrates the ultrasonic probe 404 viewed from the horizontal direction, the direction perpendicular to the vertical direction referred to in FIGS. 3A and 3B. FIG. 4A also illustrates the transmission member 502 extending from the ultrasonic probe 404, extending within the sheath 304, and connecting to the transducer 312. The ultrasonic probe 404 and transmission member 502 are in its stationary state, a state where neither the ultrasonic vibration nor the high frequency current is applied to the ultrasonic probe 404 and transmission member 502. FIG. 4B also illustrates the ultrasonic probe 404 viewed from the horizontal direction. FIG. 4B illustrates an exaggerated representation of the ultrasonic probe 404 and the transmission member 502 in an oscillating state, i.e., a state where the ultrasonic vibration is applied. Because the ultrasonic probe 404 is not curved in the vertical direction, axial unbalance in the vertical direction is minimal compared to the axial unbalance due to the curved ultrasonic probe 404 curving in the horizontal direction. Thus, the undesired transverse vibrations that may occur at the antinode 504 at the time of application of ultrasonic vibration is weak compared to the transverse vibrations in the horizontal direction as disclosed in FIG. 3B. FIG. 5 also illustrates an exaggerated representation of the ultrasonic probe 404 and the transmission member 502 in its perspective view. FIG. 5 illustrates the ultrasonic probe 404 and transmission member 502 in its oscillated state, showing the occurrence of undesired transverse vibration created due to the curve of the ultrasonic probe 404.

Figure 6:
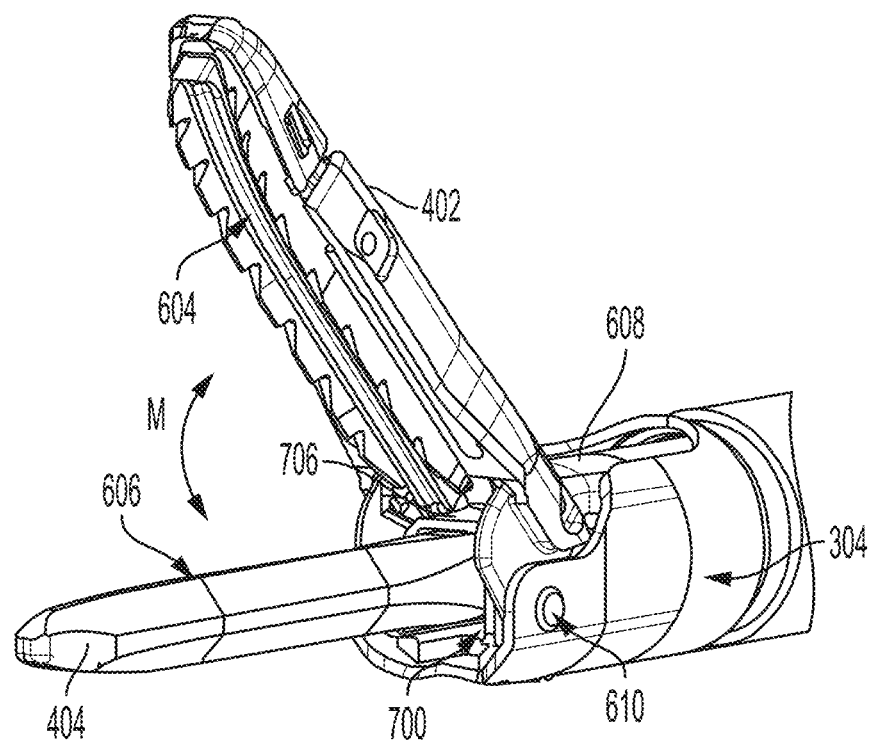
FIG. 6 is a magnified schematic view of the treatment end of the treatment device with the jaw in an open position and showing aspects of the probe holder structure.

FIG. 6 is a perspective view of the treatment end 306 of the surgical treatment device 300 in an open jaw state and showing aspects of a probe holder 700. The jaw 402 includes an upper clasping surface 604 facing the ultrasonic probe 404 and the ultrasonic probe 404 includes a lower clasping surface 606 facing the jaw 402. The upper clasping surface 604 and the lower clasping surface 606 move relative to each other, typically by having jaw 402 pivot about an axis located at fulcrum 610, in order to clasp biological tissues for treatment, such as dissection and/or coagulation. The relative movement M is actuated through the operation of the moving handle 308 and a motion mechanism, such as slider 608 embedded within the sheath 304. The jaw 402 is rotatably joined to the probe holder 700 and to a sheath 304, rotatable together with sheath 304. The probe holder 700 may be made from electrically insulated materials such as resin or rubber and the inner surfaces of the probe holder 700 at least partially circumscribe the outer circumference surface of the ultrasonic probe 404. The probe holder 700 slidably holds the ultrasonic probe 404 and, as described herein, with coordinated movement of the jaw 402 in the open direction, a region 706 (also called herein an upper holding portion) of the probe holder 700 contacts a surface of the ultrasonic probe 404, either with line contact or area contact, to attenuate ultrasonic vibration including transverse vibration that causes abnormal noise and other undesirable effects, particularly when the ultrasonic probe 404 is in an unloaded state, i.e., not in contact with biological tissue and/or not in contact with the jaw 402, particularly not in contact with the upper clasping surface 604 of the jaw 402. A base end 618 of the sheath 304 is connect to or otherwise interfaces with the sheath 304.

Figure 7:
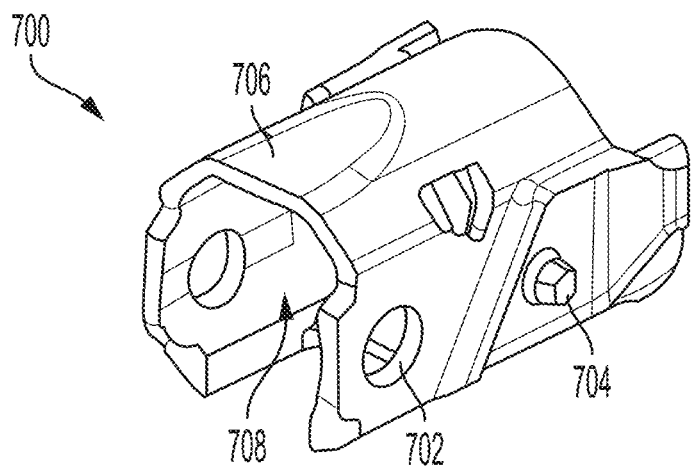
FIG. 7 is a perspective schematic view of a structure of the probe holder.

FIG. 7 illustrates the probe holder 700 unaccompanied by other portions of the treatment end 306 of the surgical treatment device 300. The hole 702 in the probe holder 700 receives the fulcrum 610 or other structure in the base section of the jaw 402. The protrusion 704 provides a structure by which to connect the probe holder 700 to the sheath 304. For example, protrusion 704 can be snap-fit into a corresponding recess or hole on the inner surface of the sheath 304, particularly located in intermediate region 616 of the sheath 304

Figure 8A:
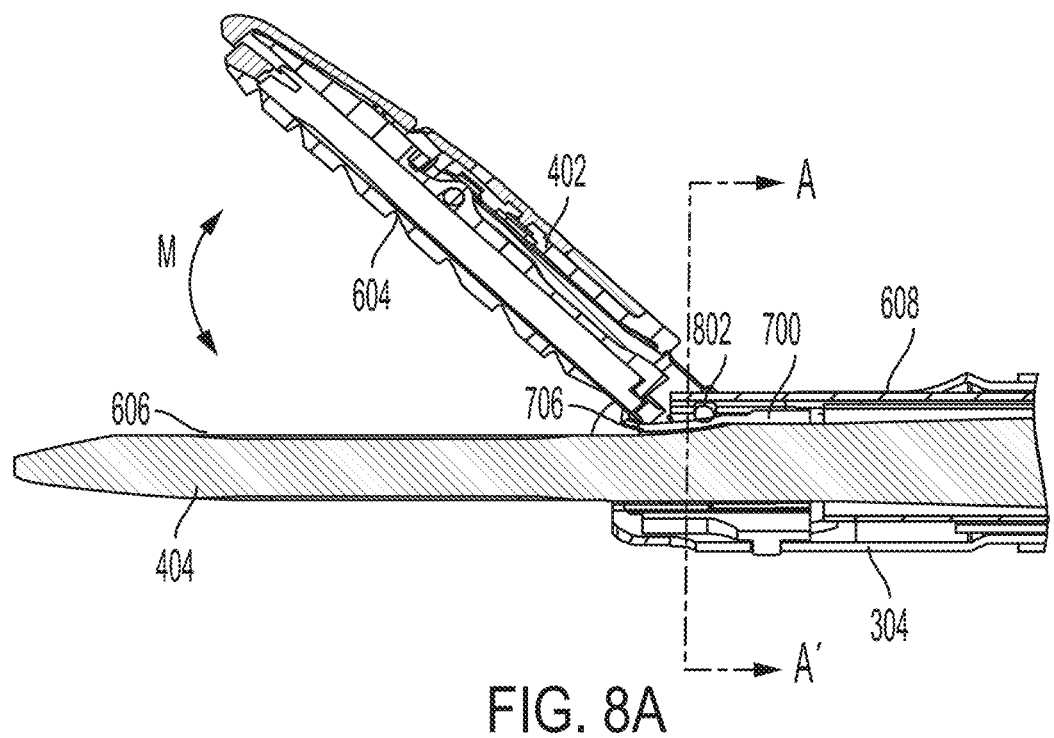
FIGS. 8A and 8B are cross-sectional side and axial views, respectively, of the treatment end of the treatment device in an open jaw state.

FIG. 8A is a cross-sectional side view of the treatment end 306 of the surgical treatment device 300 in an open jaw state. The ultrasonic probe 404 extends through the probe holder 700 and sheath 304. The jaw 402 is opened using the slider 608, which acts on fulcrum 802 to pivotably move jaw 402 about fulcrum 610 (not shown). In this open jaw position, the region 706, e.g., the upper holding portion, of the probe holder 700 is in direct contact with the surface of ultrasonic probe 404, perpendicularly as to the treatment surface, and the direct contact serving to attenuate ultrasonic vibration including transverse vibrations when the ultrasonic probe 404 is in an oscillated state. The electrical insulation of the probe holder 700 prevents electrical currents to short circuit between the ultrasonic probe 404 to the other parts of the treatment end 306, such as fulcrum 802, jaw 402, slider 608, or sheath 304 during the high-frequency current treatment procedure.

Figure 8B:
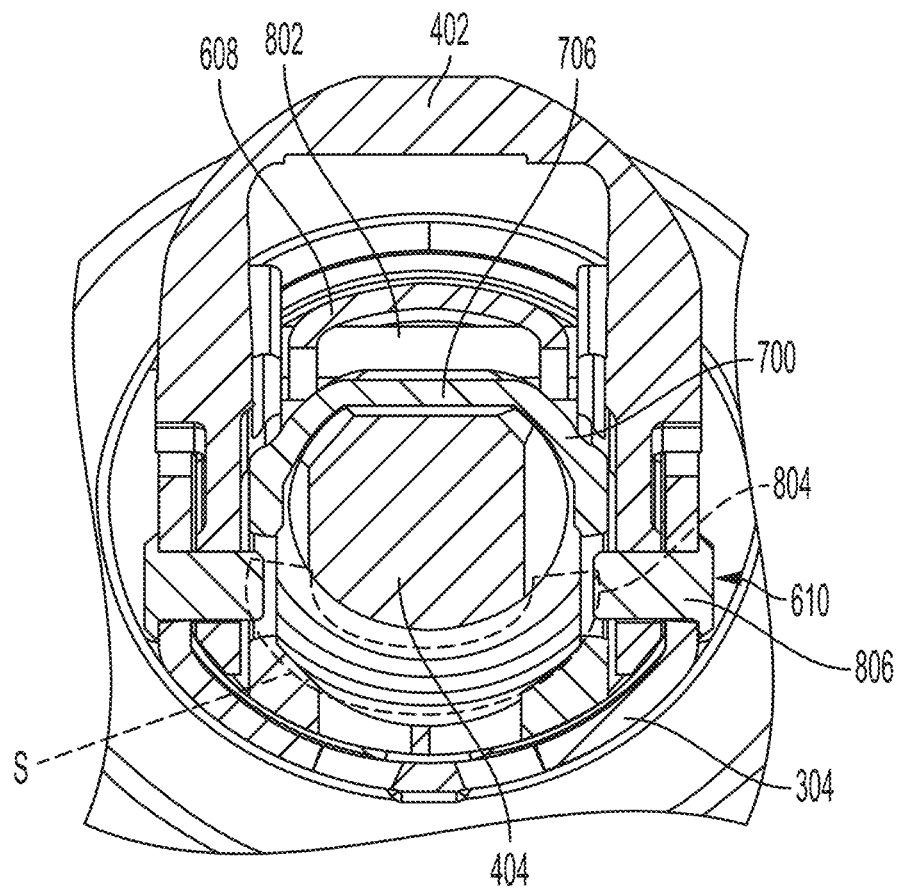

FIG. 8B is a cross-sectional axial view of the treatment end 306 of the surgical treatment device 300 in an open jaw state, viewed at the location A-A' indicated in FIG. 8A. The ultrasonic probe 404 extends through the probe holder 700 and sheath 304, which are joined together by the detents 804 and 806 on the jaw 402 at fulcrum 610. First detent 804 and second detent 806 can be integrally formed with the jaw 402 as shown in FIG. 8B, or can be separate structures affixed to the jaw 402. FIG. 8B also shows the slider 608 and fulcrum 802 that are used to open and close upper jaw 402. By not being loaded, the ultrasonic probe 404 is biased toward and contacts the region 706, e.g., the upper holding portion, of the probe holder 700, serving to attenuate ultrasonic vibration including transverse vibrations when the ultrasonic probe 404 is in an oscillated state. At the same time, the ultrasonic probe 404 is spaced apart from the probe holder 700 and sheath 304 at a circumferential location of the ultrasonic probe 404 that is 180 degrees from the location where the ultrasonic probe 404 is contacts the region 706, e.g., there is a space between the outer circumference surface of the ultrasonic probe 404 and the probe holder 700 and sheath 304 in region indicated by S in FIG. 8B.

Figure 9A:
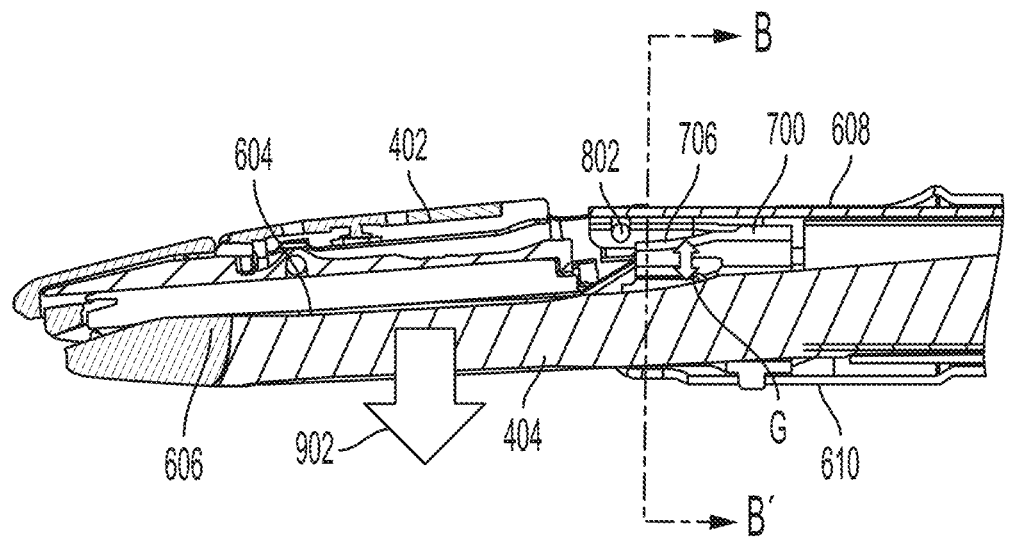
FIGS. 9A and 9B are cross-sectional side and axial views, respectively, of the treatment end of the treatment device in a closed jaw state.

FIG. 9A is a cross-sectional side view of the treatment end 306 of the surgical treatment device 300 in a close jaw state. The jaw 402 is closed using the slider 608, which acts on fulcrum 802 to pivotably move jaw 402 about fulcrum 610 (not shown). In the closed position, the upper clasping surface 604 contacts the lower clasping surface 606 of the ultrasonic probe 404 and applies a force in the downward direction 902. Due to the downward force 902 applied to the ultrasonic probe 404 by the jaw 402, the entirety of the ultrasonic probe 404 is displaced and pushed in the downward direction towards the space indicated by S in FIG. 8B, resulting in a gap (represented by arrow G) forming between the surface of the ultrasonic probe 404 and the probe holder 700. In particular, the surface of the ultrasonic probe 404 no longer contacts the region 706, e.g. the upper holding portion 706, of the probe holder 700. Since the region 706 is not in direct contact with ultrasonic probe 404 (and in contrast to the arrangement of these features in the open jaw state illustrated in FIGS. 8A-B), the attenuation of the ultrasonic vibration using the probe holder 700 does not take place. However, through direct contact of the upper clasping surface 604 and the lower clasping surface 606 or direct contact of the lower clasping surface 606 with the biological tissue(s) to be treated, attenuation of the ultrasonic probe 404 would still occur.

Figure 9B:
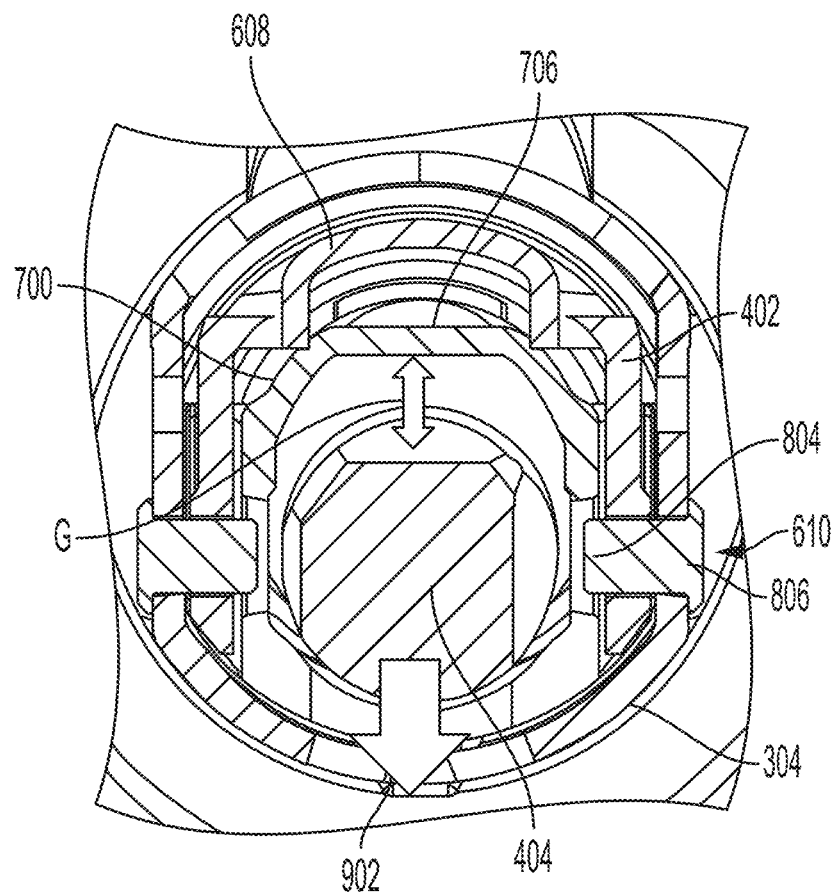

FIG. 9B is a cross-sectional axial view of the treatment end 306 of the surgical treatment device 300 in a closed jaw state, viewed at the location B-B' indicated in FIG. 9A. The jaw 402 is closed using the slider 608 acting on fulcrum 802 (not shown) to pivotably move jaw 402 about fulcrum 610. The gap G resulting from the downward force 902 discussed above is illustrated between the ultrasonic probe 404 and probe holder 700, in particular between the surface of the ultrasonic probe 404 and the region 702 (i.e. upper holding portion) of the probe holder 700. Since the upper holding portion 706 is not in direct contact with ultrasonic probe 404, the attenuation of the ultrasonic vibration using the probe holder 700 does not take place. However, through direct contact of the upper clasping surface 604 and the lower clasping surface 606 or direct contact of the lower clasping surface 606 with the biological tissue(s) to be treated, attenuation of the ultrasonic probe 404 still occurs.

Figure 10A:
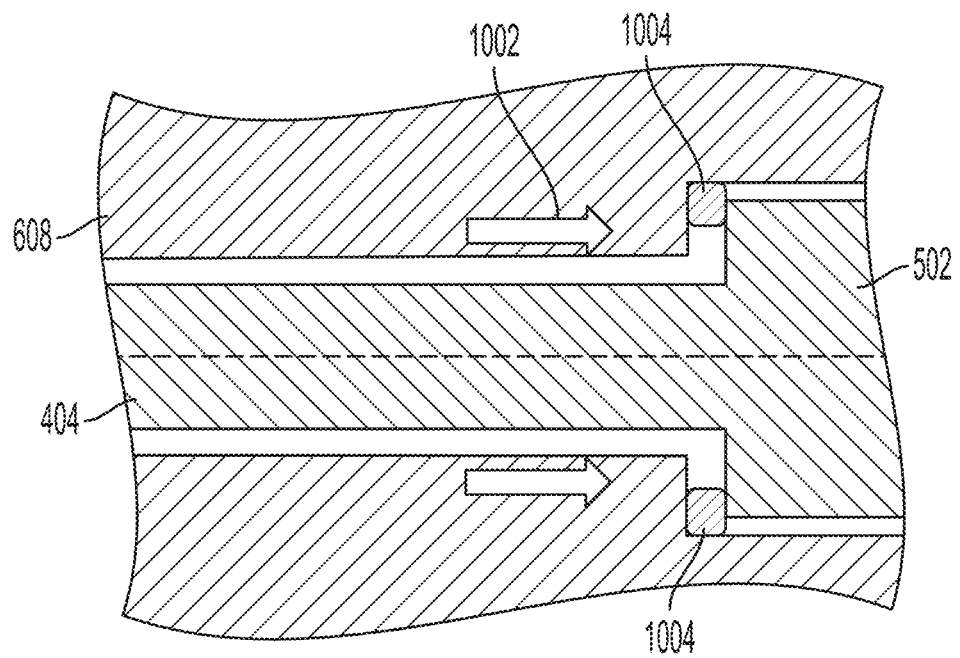
FIGS. 10A and 10B illustrate a first schema of the treatment end utilizing a damping feature associated with the drive member.

FIG. 10A schematically illustrates the internal arrangement of the slider 608 and ultrasonic probe 404 of the surgical treatment device 300 in an open jaw state of the second embodiment. At the time the jaw 402 opens, the slider 608 is moved towards the proximal direction (i.e., in the direction indicated by arrow 1002) relative to the ultrasonic probe 404. The slider 608 includes a damping feature 1004, such as an elastic cushion made from insulation materials such as rubber and resin that moves together with the slider 608. The electrical insulation of the damping feature 1004 prevents electrical currents to short circuit between the ultrasonic probe 404 to the other parts of the treatment end 306 during the high-frequency current treatment procedure. The damping feature 1004 may have a square or rectangular shape and can be affixed to the slider 608 or can be integrally formed with the slider 608. When the damping feature 1004 comes in direct contact with the thickened portion of the ultrasonic probe 404 or the transmission member 502 at the open jaw state, the transverse vibrations causing noise when the ultrasonic probe 404 is at an oscillated state will be attenuated.

Figure 10B:
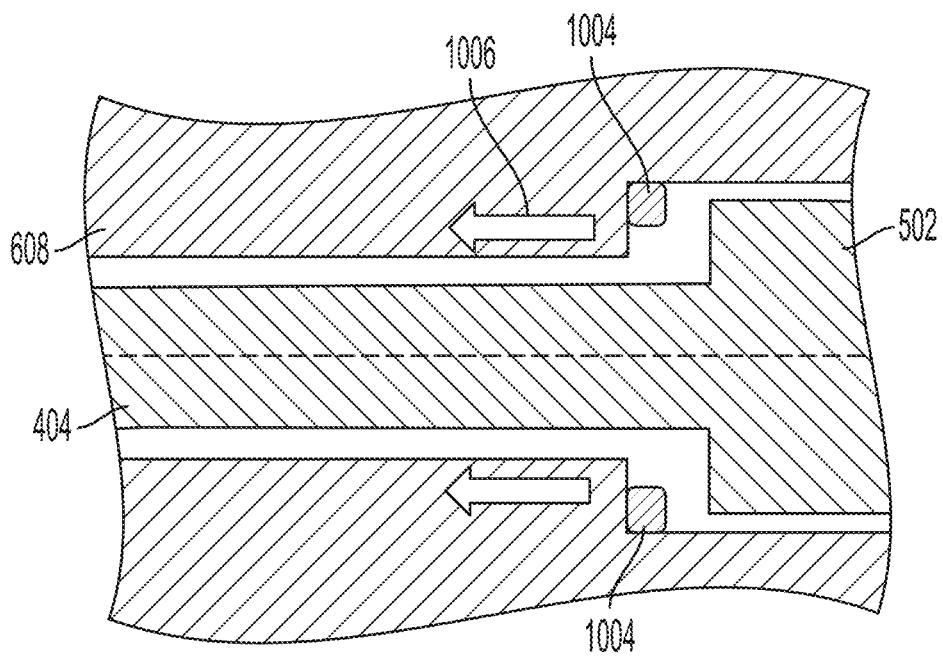

FIG. 10B schematically illustrates the internal arrangement of the slider 608 and ultrasonic probe 404 of the surgical treatment device 300 in a closed jaw state of the first embodiment. At the time the jaw 402 is closed, the slider 608 is moved towards the distal direction (i.e., in the direction indicated by arrow 1006) relative to the ultrasonic probe 404. Since the damping feature 1004 moves away from the thickened portion of the ultrasonic probe 404 or the transmission member 502 accompanying slider 608, the damping feature 1004 is spaced apart from and no longer directly contacts the ultrasonic probe 404 or the transmission member 502 and will no longer attenuate the transverse vibrations causing noise when the ultrasonic probe is at an oscillated state. However, as shown in FIGS. 9A and 9B, the attenuation of the ultrasonic probe 404 would, in this closed jaw state, be achieved through direct contact of the upper clasping surface 604 and the lower clasping surface 606 or direct contact of the lower clasping surface 606 with the biological tissue(s) to be treated.

Figure 11A:
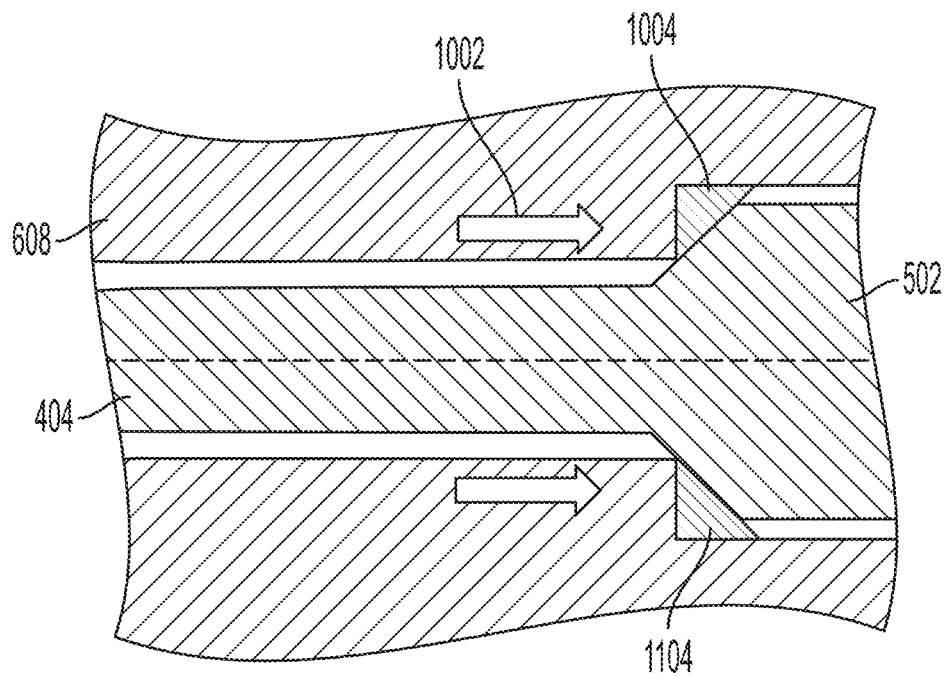
FIGS. 11A and 11B illustrate a second schema of the treatment end utilizing a damping feature associated with the drive member.

FIG. 11A schematically illustrates the internal arrangement of the slider 608 and ultrasonic probe 404 of the surgical treatment device 300 in an open jaw state of a third embodiment. At the time the jaw 402 opens, the slider 608 is moved towards the proximal direction (i.e., in the direction indicated by arrow 1002) relative to the ultrasonic probe 404. The slider 608 includes a damping feature 1004, such as an elastic cushion, that moves together with the slider 608. The damping feature 1004 may have a triangular shape and can be affixed to the slider 608 or can be integrally formed with the slider 608. This configuration allows the damping feature to contact the transmission rod and apply force in the radial direction, which may effectively attenuate transverse vibrations. When the damping feature 1004 comes in direct contact with the tapered portion of the ultrasonic probe 404 or the transmission member 502 at the open jaw state, the transverse vibrations causing noise when the ultrasonic probe 404 is at an oscillated state will be attenuated.

Figure 11B:
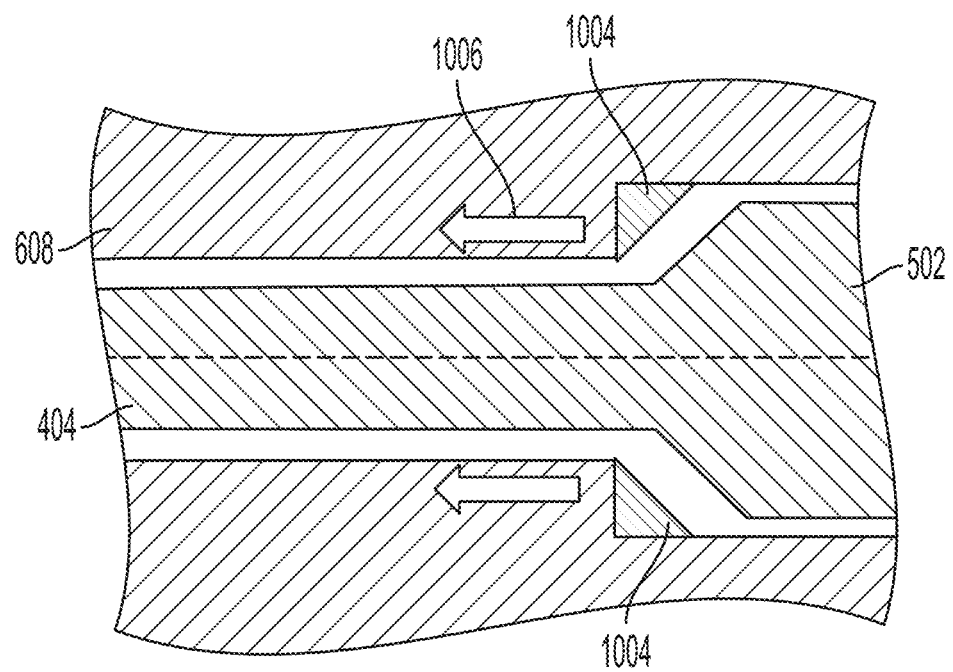
Figure 12:
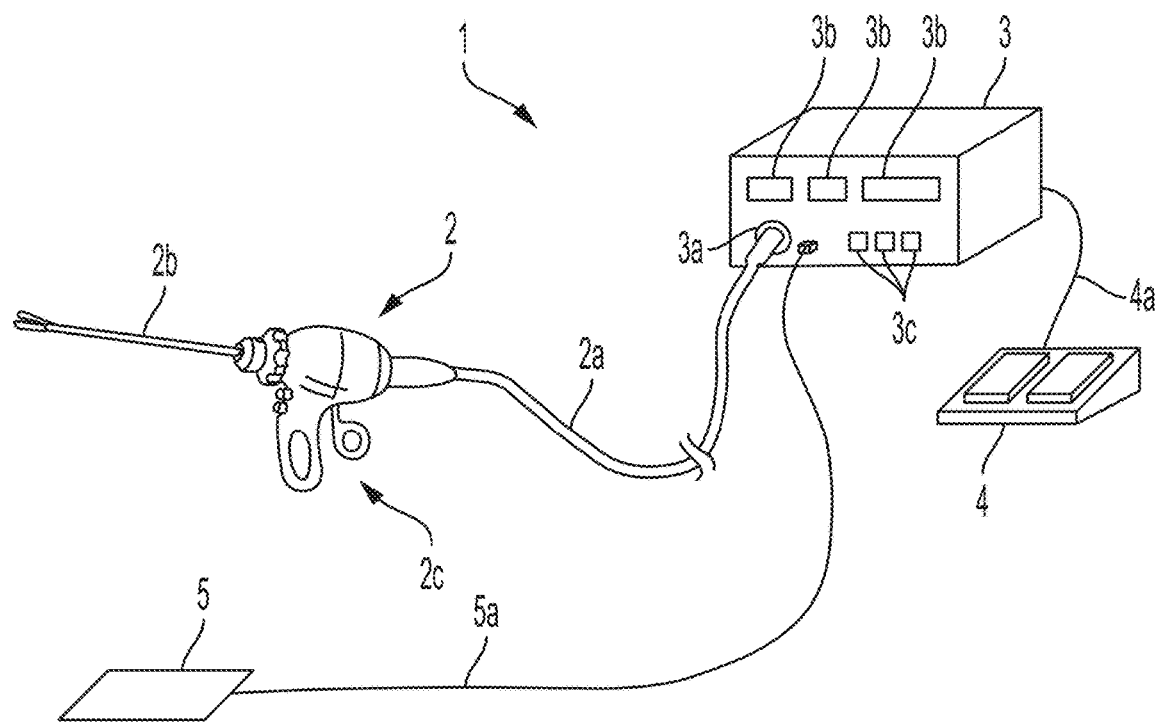
FIG. 12 shows an ultrasonic treatment device in the related art.
Figure 13:
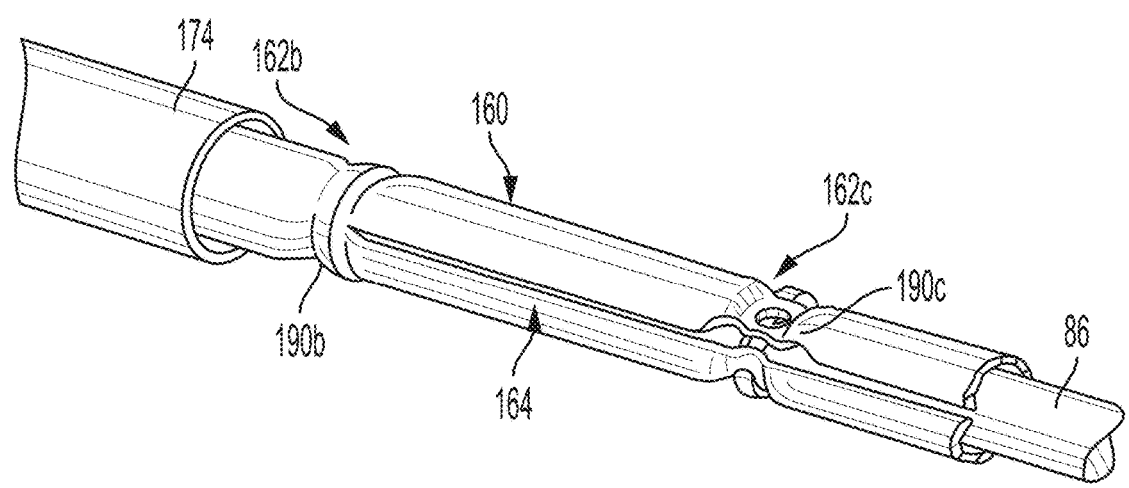
FIG. 13 shows a portion of an ultrasonic treatment device in the related art.

FIG. 11B schematically illustrates the internal arrangement of the slider 608 and ultrasonic probe 404 of the surgical treatment device 300 in a closed jaw state of the second embodiment. At the time the jaw 402 is closed, the slider 608 is moved towards the distal direction (i.e., in the direction indicated by arrow 1006) relative to the ultrasonic probe 404. Since the damping feature 1004 moves away from the ultrasonic probe 404 or the included portion of the transmission member 502 accompanying slider 608, the damping feature 1004 is spaced apart from and no longer directly contacts the ultrasonic probe 404 or the transmission member 502 and will no longer attenuate the transverse vibrations causing noise when the ultrasonic probe is at an oscillated state. However, as shown in FIGS. 9A and 9B, the attenuation of the ultrasonic probe 404 would, in this closed jaw state, be achieved through direct contact of the upper clasping surface 604 and the lower clasping surface 606 or direct contact of the lower clasping surface 606 with the biological tissue(s) to be treated.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A surgical treatment device, comprising:
a transducer generating ultrasonic vibrations;
a sheath extending along a longitudinal axis;
a transmission rod including a treatment probe, wherein a proximal end of the transmission rod is operatively connected to the transducer for transmitting ultrasonic vibration generated by the transducer to the treatment probe located at a distal end of the transmission rod, the transmission rod passing through an inside of the sheath;
a damping feature through which the transmission rod passes, the damping feature being provided on a distal end side of the sheath; and
the treatment probe including a treatment surface and a jaw moveable relative to the transmission rod from an open position to a closed position,
wherein the damping feature contacts the transmission rod when the jaw is in the open position, and
wherein the damping feature is spaced apart from the transmission rod when the jaw is in the closed position.

2. The surgical treatment device according to claim 1, wherein the damping feature is made of insulate material.

3. The surgical treatment device according to claim 1, wherein the damping feature is made of resin.

4. The surgical treatment device according to claim 1, wherein the damping feature is made of rubber.

5. The surgical treatment device according to claim 1, wherein the damping feature covers the transmission rod perpendicularly as to the treatment surface.

6. The surgical treatment device according to claim 1, where in the damping feature is placed within half wavelength of the ultrasonic vibration from the distal end of the treatment probe in the axial proximal direction.

7. The surgical treatment device according to claim 1, where in the damping feature is placed near a fulcrum of the jaw.

8. The surgical treatment device according to claim 1, wherein the transmission rod is displaced towards the direction the jaw closes in the closed position.

9. The surgical treatment device according to claim 1, wherein the contact between the damping feature and transmission rod does not occur at a node of a transverse vibration of the ultrasonic vibration.

10. The surgical treatment device according to claim 1, wherein the contact between the damping feature and transmission rod does not occur at an antinode of a longitudinal vibration of the ultrasonic vibration.

11. The surgical treatment device according to claim 1, wherein the contact between the damping feature and transmission rod occurs at an antinode of a transverse vibration of the ultrasonic vibration.

12. The surgical treatment device according to claim 1, wherein the treatment probe is configured to treat biological tissue.

13. The surgical treatment device according to claim 1, wherein the treatment probe is configured as an electrode for treatment using high frequency currents.

14. The surgical treatment device according to claim 1, wherein the damping feature prevents short circuit between the transmission rod and other parts of the treatment device.

15. The surgical treatment device according to claim 1, wherein the treatment probe includes a curved shape.

16. A surgical treatment device, comprising:
a transducer generating ultrasonic vibrations;
a sheath extending along a longitudinal axis;
a transmission rod including a treatment probe, wherein a proximal end of the transmission rod is operatively connected to the transducer for transmitting ultrasonic vibration generated by the transducer to the treatment probe located at a distal end of the transmission rod, the transmission rod passing through an inside of the sheath;
a damping feature through which the transmission rod passes, the damping feature being provided on a distal end side of the sheath;
the treatment probe including a treatment surface and a jaw moveable relative to the transmission rod from an open position to a closed position; and
a slider that moves in a direction parallel with the transmission rod,
wherein the slider and jaw are configured so that, when the slider moves towards the proximal end of the transmission rod the jaw moves in the opening direction and, when the slider moves towards the distal end of the transmission rod the jaw moves in the closing direction, wherein the damping feature contacts the transmission rod when the jaw is in the open position, and wherein the damping feature is spaced apart from the transmission rod when the jaw is in the closed position.

17. The surgical treatment device according to claim 16, wherein the damping feature has a square or rectangular shape.

18. The surgical treatment device according to claim 16, wherein the damping feature has a triangular shape.

19. The surgical treatment device according to claim 16, wherein the damping feature moves integrally with the slider.

20. A method for controlling a surgical treatment device, the method comprising:

generating ultrasonic vibrations;

connecting a transmission rod including a treatment probe to the transducer for transmitting ultrasonic vibration generated by the transducer to the treatment probe, wherein the transmission rod passes through an inside of a sheath extending along a longitudinal axis; and moving a jaw relative to the treatment surface of the transmission rod for opening and closing, wherein the transmission rod passes through a damping feature provided on a distal end side of the sheath, wherein a damping feature contacts the transmission rod when the jaw is in the open position, and wherein the damping feature is spaced apart from the transmission rod when the jaw is in the closed position.

* * * * *